United States Patent [19]

Cooper et al.

[11] Patent Number: 4,692,608
[45] Date of Patent: Sep. 8, 1987

[54] COMPACT OPTICAL IMAGING SYSTEM

[75] Inventors: David H. Cooper, Saratoga, Calif.; Makoto Toyota; Satoshi Arakawa, both of Omiya, Japan

[73] Assignee: Fuji Photo Optical Company, Ltd., Uetake, Japan

[21] Appl. No.: 611,618

[22] Filed: May 18, 1984

[51] Int. Cl.$^4$ .............................................. H01J 3/14
[52] U.S. Cl. .................................. 250/216; 250/578; 250/276; 128/4; 128/6
[58] Field of Search ................ 250/201 AF, 204, 578, 250/201 PF, 226, 216; 128/4, 6; 354/402–404, 406; 356/4

[56] References Cited

U.S. PATENT DOCUMENTS

| 3,595,220 | 7/1971 | Kawahara | 128/6 |
| 3,817,619 | 6/1974 | Kawahara | 128/6 |
| 3,901,220 | 8/1975 | Koyasu et al. | 128/6 |
| 4,132,888 | 1/1979 | Kondo | 250/204 |
| 4,153,834 | 5/1979 | Hayamizu | 250/201 AF |
| 4,163,149 | 7/1979 | Sawano et al. | 250/204 |

Primary Examiner—Norman Morgenstern
Assistant Examiner—Janyce A. Bell
Attorney, Agent, or Firm—Michael L. Harrison

[57] ABSTRACT

A compact optical imaging system with application to a viewing head of an endoscope. A lens assembly gathers and focuses light into parallel rays which are turned 90° from the lens assembly optical axis. A planar image sensor is oriented parallel to the lens assembly optical axis and receives the light which has been turned. The light enters a glass plate serving as the back side of the image sensor and impinges on active light-sensitive elements on a silicon layer deposited on the glass plate. A substrate is bonded on the silicon layer and supports circuitry for buffering and driving signals to and from the image snsor. The substrate has a plurality of slots aligned with the bonding pads of the image sensor to permit electrical connection between the buffering and driving circuitry and the image sensor.

23 Claims, 4 Drawing Figures

COMPACT OPTICAL IMAGING SYSTEM

BACKGROUND OF THE INVENTION

This invention relates to compact optical imaging systems, and in particular to compact viewing heads in the insertion tubes of color video endoscope systems.

In color video endoscope systems the insertion tube of the endoscope includes a fiber optic light guide for directing light into the cavity to be viewed, an optical focusing section for gathering and focusing the reflected light, an image sensor for providing electrical output in response to the light input, electrical circuitry and connection means for triggering the image sensor and for transmitting signals back to a control unit, a biopsy channel, and water and air delivery channels. Because these features must all be present in the insertion tube of the endoscope and because the overall diameter of the insertion tube is limited by the human anatomy, it is important to optimize space utilization in the insertion tube.

In conventional color video endoscope systems the viewing head or imaging system at the distal end of the insertion tube usually comprises an optical focusing section and a solid state rectangular image sensor oriented perpendicular to the optical axis of the imaging system and to the central axis of the insertion tube. Associated circuitry to buffer the input to the image sensor and drive the output is separately supported and mounted in close proximity and behind the light-receiving face of the image sensor. Because the image sensor in such endoscopes is oriented perpendicular to the optical axis, the size of the image sensor is limited. In addition, since the image sensor provides a rectangular surface area greater than the circular surface area of the optical focusing section, it is difficult to package the biopsy channel, light guide and other features required to be contained within the insertion tube.

SUMMARY OF THE INVENTION

The present invention is a compact optical imaging system with specific application to color video endoscopy which maximizes the space utilization in the insertion tube.

Unlike conventional viewing heads in use in color video endoscopes, the image sensor of the present invention is oriented with its plane other than perpendicular to the axis of the optical focusing section, preferably parallel to the optical axis. The invention includes means for turning the light away from the optical axis so that the light rays impinge on the image sensor. In a preferred embodiment the image from the focusing section is turned 90° to the image sensor by a glass wedge having a surface for internal reflection.

By placement of the image sensor in a plane parallel to the optical axis, an image sensor substantially larger than the diameter of the optical focusing section can be utilized. In particular, a frame-transfer image sensor which utilizes at least two registers, a register for receiving an image directly from the optical focusing section, and a second register for transfer of data from the first register, can be used in the viewing head. In the embodiment of the present invention, a preferred image sensor is a back-lighted frame-transfer image sensor in which the incident light passes through a thin glass plate before impinging on the active elements of the image sensor. The glass plate of the image sensor is bonded directly to the light output surface of the glass wedge. A substrate supporting the circuit elements of the buffer/driver circuitry for the image sensor can be bonded directly to the face of the back-lighted image sensor which contains the active elements. Slots are provided in the substrate which are oriented in alignment with the bonding pads of the image sensor so that electrical connection can be made between the circuit elements on the substrate and the image sensor.

The present invention thus provides a viewing head in the insertion tube of an endoscope which optimizes space utilization and permits the use of a substantially larger image sensor and the support of associated electrical circuitry.

DESCRIPTION OF THE PREFERRED EMBODIMENTS

Figure 1:
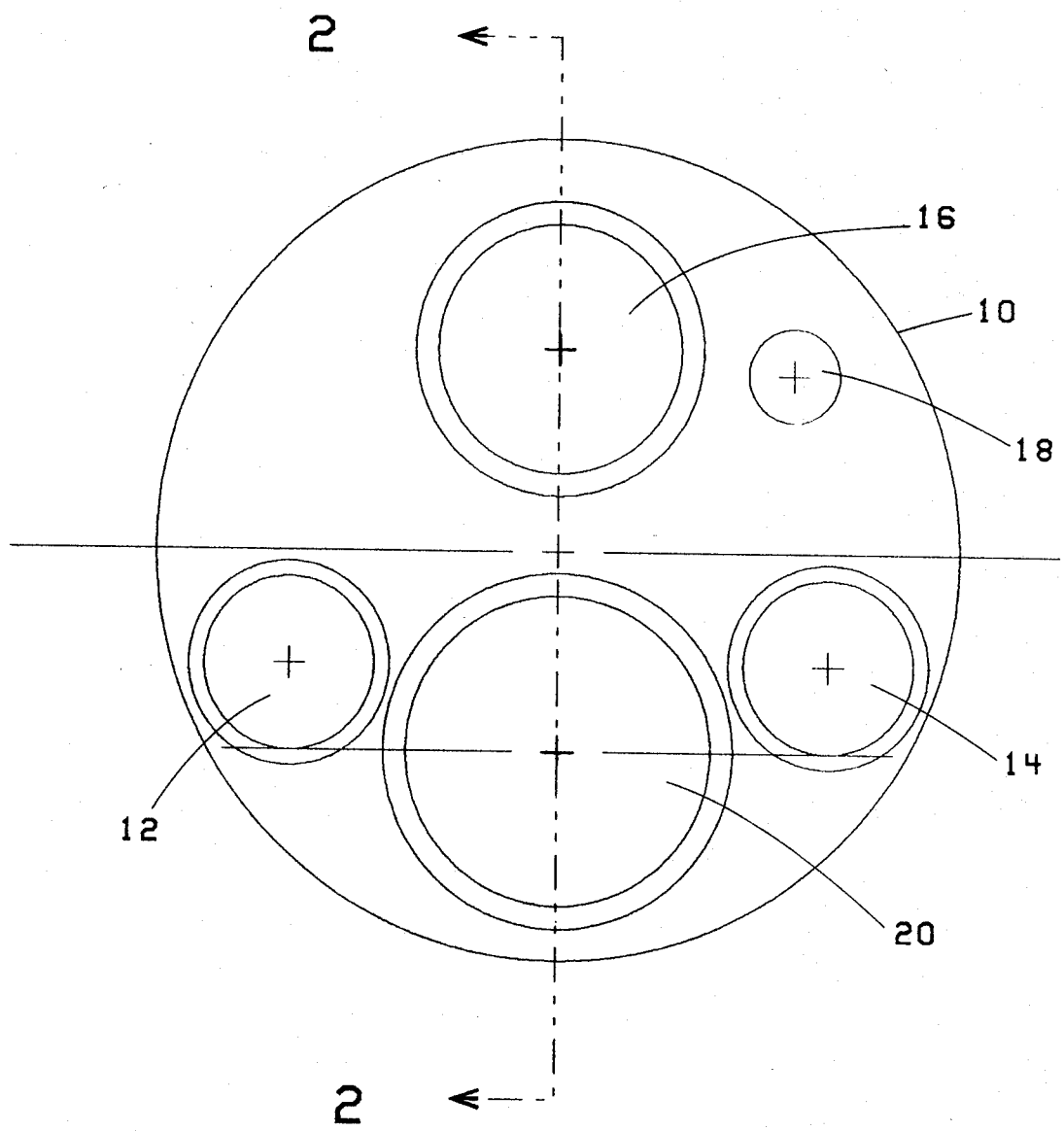
FIG. 1 is a view of the front end of the viewing head of the endoscope.

Referring first to FIG. 1, the various components present in the viewing head of an endoscope are illustrated. As illustrated in this front view of the distal end of the endoscope insertion tube 10, which is the end inserted into the cavity to be observed, are light output guides 12, 14, a biopsy channel 16, an air/water channel 18, and the optical focusing section 20 for gathering and focusing the reflected light from the cavity.

Figure 2:
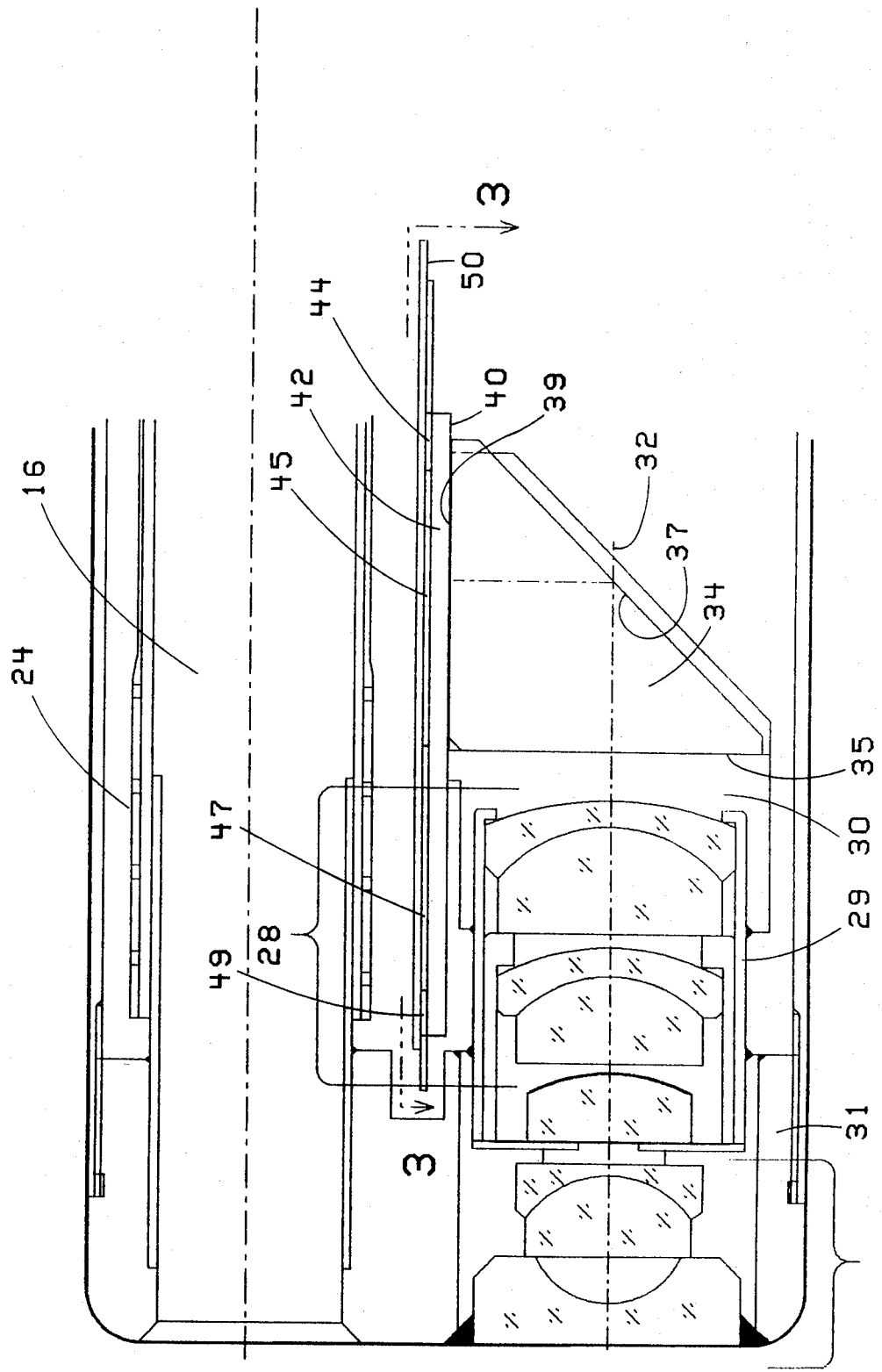
FIG. 2 is a sectional view of view 2—2 of FIG. 1.

Referring now to FIG. 2, which is a vertical section of view 2—2 of FIG. 1, there is illustrated the biopsy channel 16 with a surrounding cylindrical metal sheath 24, and the lens assembly for gathering the reflected light from the cavity and focusing it to the image sensor 40. The lens assembly comprises an objective lens assembly 26, which provides a field of view of approximately 120°, and a focusing lens assembly 28 which takes the light from the objective lens assembly and focuses it into an image which is ultimately turned 90° to form an image on image sensor 40. The objective lens assembly 26 and focusing lens assembly 28 have a common optical axis 32. The individual lens elements of focusing assembly 28 are held together by a frame 29 which is attached to the exterior surface 31 of the viewing head. The light rays 30 from focusing assembly 28 are turned away from optical axis 32 by a glass wedge 34 which has a light input face 35, a surface 37 which causes internal reflection of light rays 30, and a light output face 39.

The image sensor 40 is shown in edge view in FIG. 2 with its planar surface generally parallel to optical axis 32. The image sensor 40 is a frame-transfer charge-coupled device (CCD) which comprises a thin glass plate 42 and a silicon layer 44 containing the active light-sensitive elements deposited onto glass plate 42. A typical frame-transfer CCD is an RCA model SID 504 which has three registers, each register comprising an array of light-sensitive elements or pixels. The A register 45, which is aligned with the light output surface 39 of glass wedge 34, is adjacent to the B register 47. A horizontal shift register 49 is located at the end of CCD 40. The light which is gathered by objective lens assembly 26, converted into an image by focusing lens assembly 28 which is then turned 90° by glass wedge 34, strikes the pixel elements present in the A register 45 after passing through the glass plate 42 of CCD 40. While the CCD 40 is rectangular in shape, the image formed on the A register 45 is circular because of the circular elements of objective lens assembly 26.

Figure 3:
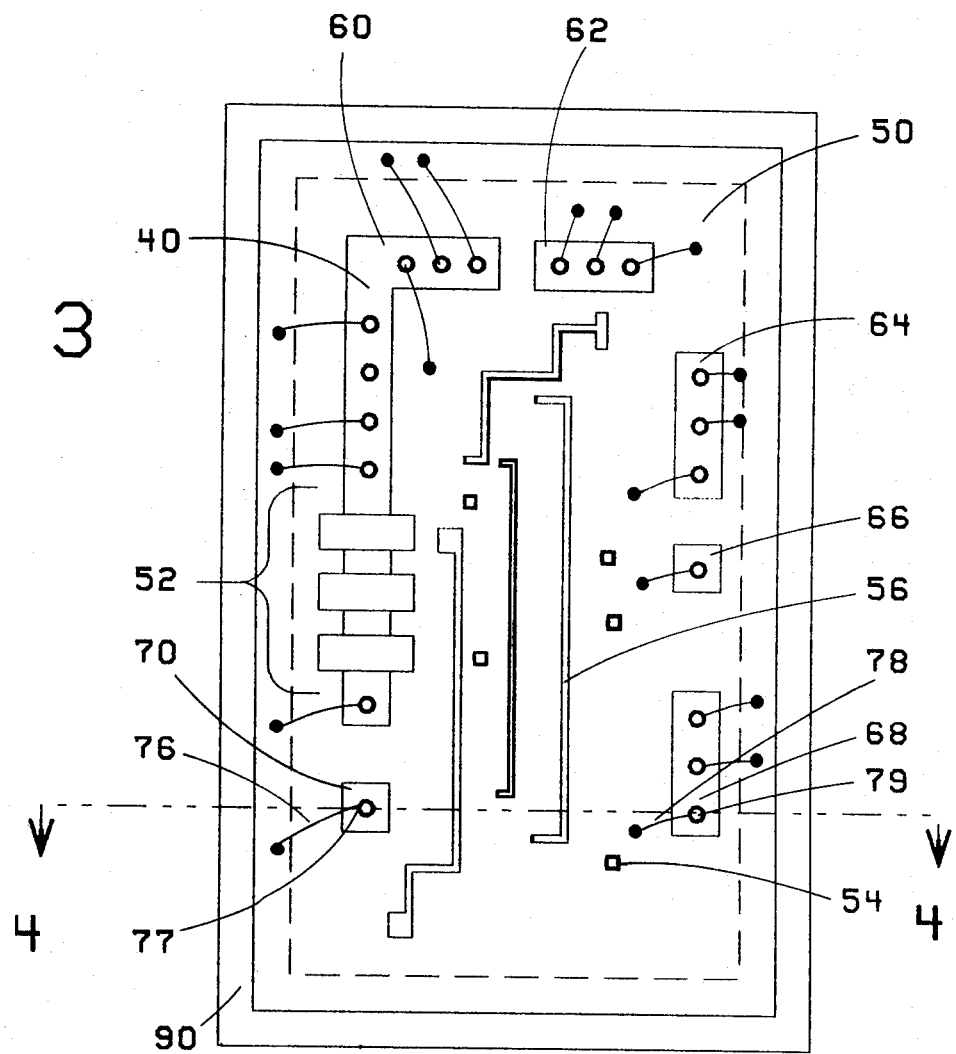
FIG. 3 is a view of view 3—3 of FIG. 2 illustrating a top view of the substrate and the bonding pads of the image sensor.
Figure 4:
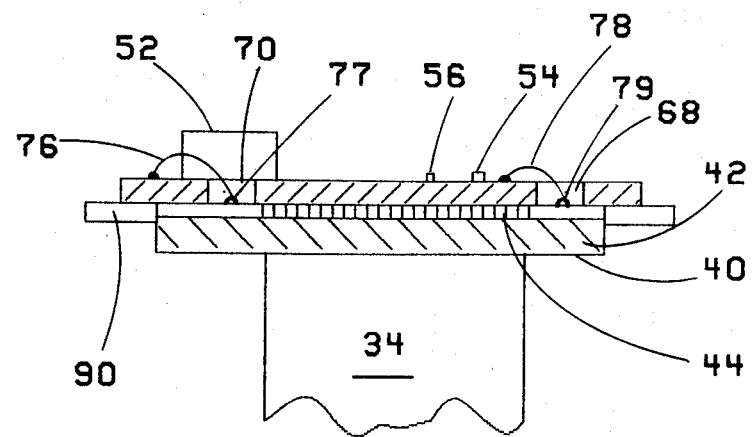
FIG. 4 is a view of view 4—4 of FIG. 3 illustrating a sectional view of the substrate, image sensor and glass wedge bonded together.

The image sensor 40 is required to be electrically coupled to a control unit (not shown) connected to the endoscope. Electrical circuitry is required to buffer the input pulses from the control unit which clock out the charges stored on the image sensor and to amplify the image sensor output signals back to the control unit. In the present invention this electrical circuitry comprises discrete integrated circuit components which are supported on a ceramic substrate 50, as illustrated in FIGS. 3 and 4. FIG. 3 is a view of 3—3 of FIG. 2 and illustrates a portion of the circuitry supported on substrate 50, including capacitors 52, transistor elements 54 and circuit traces 56. Also shown in FIGS. 3 and 4 is CCD 40 having a number of bonding pads, such as bonding pads 77, 79, around its perimeter beyond the active light sensitive elements on silicon layer 44. The substrate 50 includes a plurality of slots, such as slots 60, 62, 64, 66, 68, and 70. These slots, which are cut into the substrate 50 by laser or other means, permit electrical connection to be made from the active circuit elements on substrate 50 down to the bonding pads, such as bonding pads 77, 79 of CCD 40.

FIG. 4 is a sectional view of view 4—4 of FIG. 3 and illustrates the substrate 50 bonded directly to the active silicon layer 44 of image sensor 40. The slots shown in FIG. 4 in sectional view, namely slots 68, 70, permit electrical wire bonds 76, 78 to make connection between bonding pads 77, 79 on CCD 40 and circuit elements on substrate 50.

Referring again to FIG. 2, the glass wedge 34 is bonded directly to the glass plate 42 of CCD, and substrate 50 is bonded directly to the active silicon layer 44 of CCD 40. Optical quality epoxy is used for this purpose. The glass wedge 34 is attached to the frame 29 of focusing assembly 28 and is thus held in fixed spatial relationship with the objective and focusing lens assemblies 26, 28. In this manner the lens assembly serves as a support structure for the CCD, which in turn serves as a support structure for the associated circuitry present on the substrate 50. Because the image sensor 40 is oriented other than perpendicular to the optical axis 32, a substantially larger image sensor can be used, in this case a frame-transfer image sensor which requires a substantially larger surface area than other types of image sensors. In addition, because slots in the substrate 50 are aligned with the bonding pads on the perimeter of the image sensor 40, it is possible to make electrical connections directly between the image sensor and active circuit elements supported on the substrate 50.

Substrate 50 may be further supported in spatial relationship to CCD 40 by means of a frame 90 (FIG. 5) which overlays the rectangularly shaped CCD about its perimeter. Substrate 50 is secured to frame 90, as well as to CCD 40, in order to insure that the substrate 50 and CCD 40 do not move relative to one another, which could cause breaking of wire bonds, such as wire bonds 76, 78.

In the present invention, the integrated construction of the image sensor, substrate and glass wedge allows the image sensor and associated circuitry to be provided in the relatively limited space between the lens assembly and biopsy channel 16 of the endoscope viewing head. It should be apparent from FIG. 2 that if the frame-transfer CCD and associated circuitry on substrate 50 were oriented perpendicular to the optical axis 32, as in conventional endoscopes, a CCD of the desired size would not fit within the available space.

While the preferred embodiments of the present invention have been illustrated in detail, it should be apparent that modifications and adaptations of those embodiments will occur to those skilled in the art. However, it is to be expressly understood that such modifications and adaptations are within the sphere and scope of the present invention as set forth in the following claims.

What is claimed is:

1. A compact optical imaging system comprising:
   a lens assembly for gathering and focusing light from objects within the field of view of the lens;
   an image-forming sensor having a signal output corresponding to the intensities and colors of patterns of light falling on the sensor, oriented in a plane other than perpendicular to the optical axis of the lens assembly;
   means for directing light from the lens assembly to cause the light to strike the image-forming sensor, and;
   means for supporting the lens assembly, light directing means and image-forming sensor such that the image-forming sensor is placed in the focal plane of the optical system formed by the lens assembly and the light directing means.

2. The imaging system according to claim 1 wherein the light directing means further comprises means for focusing the light and means for turning the light rays to strike the image sensor.

3. The imaging system according to claim 2 wherein the turning means further comprises a a glass wedge having a surface for internal reflection of the incident light.

4. A compact optical imaging system comprising:
   a lens assembly for gathering and focusing the light;
   a planar-shaped image sensor oriented in a plane other than perpendicular to the optical axis of the lens assembly;
   a wedge of optical material having a surface for internal reflection of light, one face of which is attached directly to the image sensor, for causing the light rays incident on another face of the wedge to be directed to the image sensor, and;
   means for retaining the lens assembly, light directing means and image sensor in a fixed spatial relationship.

5. The imaging systems according to claim 4 wherein the image sensor is back-lighted, and wherein the wedge is bonded directly to the back side of the image sensor.

6. The imaging system according to claim 4 wherein the image sensor is a frame-transfer image sensor having at least two registers, and wherein the supporting means includes means for supporting the image sensor relative to the light directing means such that the light strikes only one of the registers.

7. The imaging system according to claim 4 further comprising means for supporting electrical circuitry for buffering the input to the image sensor and driving the output from the image sensor.

8. The apparatus according to claim 7 wherein the circuitry supporting means is a substrate attached to the image sensor in a face-to-face orientation.

9. The imaging system according to claim 8 wherein the image sensor includes a plurality of bonding pads around its perimeter providing electrical connection to the image sensor, and wherein the substrate includes a plurality of slots permitting electrical connection between the bonding pads of the image sensor and circuit elements supported on the substrate.

10. A compact optical imaging system comprising:
an objective lens assembly for gathering light from objects within the field of view of the lens;
a focusing lens assembly oriented with its optical axis coincident with the optical axis of the objective lens assembly for focusing light gathered by the objective lens assembly;
means for turning the light away from the optical axis of the objective and focusing lens assemblies, and;
an image-forming sensor having a signal output corresponding to the intensities and colors of patterns of light falling on the sensor, oriented generally parallel to the optical axis of the objective and focusing lens assemblies, and;
means for supporting the image-forming sensor in a position relative to the lens assemblies such that the image sensor is placed in the focal plane of the optical system formed by the lens assemblies and the light turning means.

11. A compact optical imaging system comprising:
an objective lens assembly for gathering light from objects within the field of view of the lens;
a focusing lens assembly oriented with its optical axis coincident with the optical axis of the objective lens assembly for focusing light gathered by the objective lens assembly;
a wedge of optical material having a light input surface, a surface for internal light reflection, and a planar light output surface, and;
a backlighted, planar image sensor oriented generally parallel to the optical axis of the objective and focusing lens assemblies, said image sensor having its back side bonded to the planar light output surface of the wedge, and;
means for supporting the image sensor and wedge in a position relative to the lens assemblies such that the sensor is placed in the focal plane of the optical system formed by the lens assemblies and the wedge.

12. The imaging system according to claim 11 wherein the image sensor has light-sensitive elements bonded to a glass plate, the imaging system further comprising a planar substrate for supporting electrical circuitry for buffering input to the image sensor and driving output from the image sensor, the substrate being bonded over the light-sensitive elements of the image sensor and having a plurality of slots for electrical connection between the image sensor and circuit elements supported on the substrate.

13. The imaging system according to claim 12 wherein the glass plate of the imaging system is bonded to the light turning means.

14. A compact optical imaging system comprising:
a lens assembly for gathering and focusing light from objects within the field of view of the lens;
a back-lighted image sensing array oriented in a plane other than perpendicular to the optical axis of the lens assembly;
means bonded directly to the back side of the image sensor for directing light from the lens assembly to cause it to be be directed to the iamge sensing array, and;
means for supporting the lens assembly, light directing means and image sensing array such that the image sensing array is placed in the focal plane of the optical system formed by the lens assembly and the light directing means.

15. The imaging system according to claim 14 further comprising means for supporting electrical circuitry for buffering the input to the image sensing array and driving the output from the image sensor.

16. A compact optical imaging system comprising:
a lens assembly for gathering and focusing light from objects within the field of view of the lens;
an image-forming sensor array having a signal output corresponding to the intensities and colors of patterns of light falling on the sensor, oriented in a plane other than perpendicular to the optical axis of the lens assembly;
means for directing light from the lens assembly to cause it to be be directed to the image-forming sensor array, and;
means for supporting the lens assembly, light directing means and image-forming sensor array such that the image sensing array is placed in the focal plane of the optical system formed by the lens assembly and the light directing means.

17. A compact optical imaging system comprising:
an objective lens assembly for gathering light from objects within the field of view of the lens;
a focusing lens assembly oriented with its optical axis coincident with the optical axis of the objective lens assembly for focusing light gathered by the objective lens assembly;
means for turning light away from the optical axis of the lens assemblies, and;
a backlighted, planar image sensing array oriented generally parallel to the optical axis of the lens assemblies, said image sensing array, and;
means for supporting image sensing array in a position relative to the lens assemblies such that the array is placed in the focal plane of the optical system formed by the lens assemblies and the light turning means.

18. The imaging systems according to claim 16 wherein the image sensing array is back-lighted, and wherein the wedge is bonded directly to the back side of the image sensor.

19. The imaging system according to claim 16 wherein the image sensing array is a frame-transfer image sensing array having at least two registers, and wherein the retaining means includes means for retaining the image sensing array relative to the light directing means such that the light strikes only one of the registers.

20. The imaging system according to claim 17 wherein the image sensing array has light-sensitive elements bonded to a glass plate, the imaging system further comprising a planar substrate for supporting electrical circuitry for buffering input to the image sensing array and deriving output from the image sensor, the substrate being bonded over the light-sensitive elements of the image sensing array and having a plurality of slots for electrical connection between the image sensing array and circuit elements supported on the substrate.

21. A compact optical imaging system comprising:

a lens assembly for gathering and focusing light from objects within the field of view of the lens;

an image-forming sensor having a signal output corresponding to the intensities and colors of patterns of light falling on the sensor, oriented in a plane other than perpendicular to the optical axis of the lens assembly;

a wedge of optical material having a surface for internal reflection of light, one face of which is attached directly to the image sensor, for causing the light rays incident on another face of the wedge to be directed to the image sensor, and;

means for supporting the lens assembly, light directing means and image sensor such that the image sensor is placed in the focal plane of the optical system formed by the lens assembly and the light directing means.

22. A compact optical imaging system comprising:

a lens assembly for gathering and focusing light from objects within the field of view of the lens;

a frame-transfer image sensing array having at least two registers, oriented in a plane other than perpendicular to the optical axis of the lens assembly;

means for directing light from the lens assembly to cause it to be be directed to the image sensing array, and;

means for supporting the lens asembly, light directing means and image sensing array such that the image sensing array is placed in the focal plane of the optical system formed by the lens assembly and the light directing means, and so that the light strikes only one of the registers.

23. A compact optical imaging system comprising:

a lens assembly for gathering and focusing light from objects within the field of view of the lens;

an image-forming sensor having a signal output corresponding to the intensities and colors of patterns of light falling on the sensor, oriented in a plane other than perpendicular to the optical axis of the lens assembly;

means for directing light from the lens assembly to cause it to be be directed to the image-forming sensor;

means for supporting the lens assembly, light directing means and image-forming sensor such that the image-forming sensor is placed in the focal plane of the optical system formed by the lens assembly and the light directing means, and;

means for supporting electrical circuitry for buffering the input to the image-forming sensor and driving the output from the image-forming sensor.

* * * * *